United States Patent [19]

Ekström et al.

[11] 4,273,366
[45] Jun. 16, 1981

[54] TWO-PART FLUID CONDUIT WITH MEANS FOR CONNECTING THE SECTIONS THEREOF

[75] Inventors: Olov Ekström, Brottby; Kenth Nilsson, Akersberga, both of Sweden

[73] Assignee: Siemens Aktiengesellschaft, Berlin & Munich, Fed. Rep. of Germany

[21] Appl. No.: 887,480

[22] Filed: Mar. 17, 1978

[30] Foreign Application Priority Data

Apr. 5, 1977 [DE] Fed. Rep. of Germany ....... 2715270

[51] Int. Cl.³ ............................................. F16L 25/00
[52] U.S. Cl. .................................... 285/332; 285/384; 138/37
[58] Field of Search .................... 285/386, 332, 332.2, 285/332.3, 184; 138/37

[56] References Cited

U.S. PATENT DOCUMENTS

| 510,997 | 12/1893 | Smith | 138/37 X |
| 1,386,210 | 8/1921 | Thomas | 285/332 X |
| 1,403,773 | 1/1922 | Hanson | 285/332 |
| 1,572,355 | 2/1926 | Grote | 285/332 X |
| 2,489,100 | 11/1949 | Marco | 285/184 |
| 3,955,835 | 5/1976 | Farrington | 138/37 |

Primary Examiner—Dave W. Arola
Attorney, Agent, or Firm—Hill, Van Santen, Steadman, Chiara & Simpson

[57] ABSTRACT

The illustrated embodiment shows helical grooves of tapering cross section in the inner walls of the interfitting ends of the conduit sections for producing a rotation of the fluid as it enters and leaves the space between the annular terminal surface of one conduit end and the confronting interior ledge of the other. Because of the rotation any air bubbles are removed during filling of the conduit. For particularly vigorous rotation the annular terminal surface and/or interior ledge may be formed obliquely to the flow axis.

5 Claims, 1 Drawing Figure

U.S. Patent   Jun. 16, 1981   4,273,366
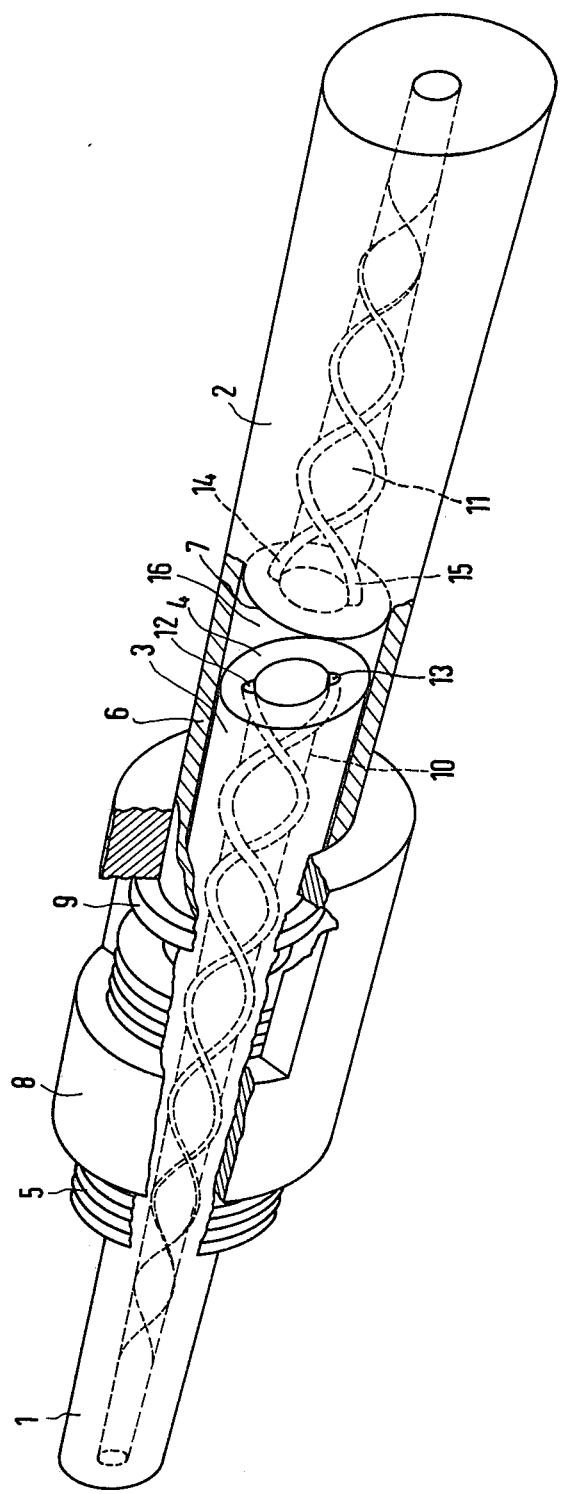

TWO-PART FLUID CONDUIT WITH MEANS FOR CONNECTING THE SECTIONS THEREOF

BACKGROUND OF THE INVENTION

The invention relates to a two-part fluid conduit comprising means for providing a sealed connection of the conduit sections where the end of the first conduit section is tapered externally and provided with an annular terminal surface, where the second conduit section is provided with an internally conical extension tapering from its end, a graduated ledge being present at the interior thereof at which the fluid conduit terminates, and the ends of the conduit sections so interfitting that with a tight connection thereof the annular terminal surface is in spaced relation from the graduated ledge.

A fluid conduit of this kind is used for example for pressure readings of body fluids and it is provided with a conduit section leading to the patient, and a conduit section connected with said first section leading to a piezometer. Prior to taking a reading the conduit sections are filled with a coupling fluid which transmits the pressure to be read from the patient to the piezometer. In this connection it is of paramount importance that the fluid conduit is filled free from air with coupling fluid, because air bubbles in the fluid conduit will produce adulterated readings. In addition, air bubbles will endanger the patient. An interstice is present in a fluid conduit of the initially mentioned type, wherein air bubbles can form, between the annular terminal surface of the first conduit section and the graduated ledge.

SUMMARY OF THE INVENTION

The invention is based on the problem of creating a fluid conduit of the initially mentioned type which assures an air-free filling.

According to the invention this problem is solved in that the inner wall of at least one of the conduit sections is provided in the area of the end to be connected with at least one helical groove. Because of the design of the inner wall the fluid is caused to rotate as the conduit is filled and because of the rotation any air bubbles possibly present at the point of connection are flushed loose and conveyed out.

In one advantageous embodiment of the invention it is suggested that the annular terminal surface of the first conduit section and/or the graduated ledge of the second conduit section are placed obliquely to the longitudinal axis of the conduit portion in question. This accomplishes a particularly vigorous rotation of the fluid in the interstice between the terminal surface and the ledge.

Below the invention is explained more in detail by way of an embodiment exemplified in the FIGURE of the accompanying sheet of drawings; other objects, features and advantages will be apparent from this detailed disclosure and from the appended claims.

BRIEF DESCRIPTION OF THE DRAWINGS

The single FIGURE is a diagrammatic perspective view, with portions broken away and in section to show internal construction.

DETAILED DESCRIPTION

The FIGURE represents a fluid conduit comprising a first conduit section 1 leading to a patient not shown, and a second conduit section 2 leading to a piezometer likewise not shown. The end 3 of the conduit section 1 is tapered conically on the outside and provided with an annular terminal surface 4 which is placed obliquely in relation to the longitudinal axis of the conduit part 1. A thread 5 is secured on the conduit section 1 ahead of its end 3. The conduit section 2 is provided with an extension 6 with its interior wall tapering conically inwardly from the outer open end thereof with a step-shaped or relatively steeply sloped interior ledge or shoulder 7 being present at the inner end of extension 6 in which the first conduit section 1 terminates. The interior ledge 7 is arranged obliquely to the longitudinal axis of the conduit section 2. A retaining nut 8 is positioned rotatably on the extension 6 of the conduit section 2 and retained by means of a flange 9 secured at the free end of the extension 6.

As both conduit parts 1, 2 are connected, the end of the conduit section 1 is inserted into the extension 6 of the conduit section 2 and pressed firmly there by tightening the retaining nut 8 on the thread 5, so that the mating tapering surfaces are in sealing engagement. An interstice or space 16 is present between the annular terminal surface 4 of the conduit section 1 and the interior ledge 7 of the conduit section 2. The inner walls 10 and 11 of the conduit sections 1 and 2 defining the fluid passageways therein may be of constant and equal diameter over the entire extent of walls 10 and 11, except that the inner walls 10 and 11 are provided in the area of the ends to be connected with respective pairs of helical grooves 12 to 15, the grooves extending with the same direction of rotation and with uniform (i.e. diametrical) separation, and tapering off continuously in their flow cross-section from the corresponding end.

As the fluid conduit 1, 2 is filled, fluid flows for example first through the conduit section 2 and is caused to rotate by means of the helical grooves 14, 15. Then the fluid enters the interstice 16, where the rotation is amplified by the obliquely positioned ledge 7 and the likewise obliquely positioned terminal surface 4. Any air bubbles present in the interstice 16 thus are conveyed outward with the fluid via the conduit section 1, whereby the rotation of the fluid is maintained by the grooves 12, 13.

A rotation of the fluid and outward conveying of the air bubbles present in the interstice 16 also can take place if only the fluid conduit the fluid enters first is provided with grooves. Moreover, the air bubbles can be moved outward without an obliquely disposed terminal surface 4 and/or an obliquely disposed ledge 7.

It will be apparent that many modifications and variations may be effected without departing from the scope of the novel concepts and teachings of the present invention.

We claim as our invention:

1. A two-part fluid conduit assembly comprising first and second conduit sections with proximate connected ends and each having a remote end remote from the proximate end thereof, said proximate ends having means providing a sealed connection of said conduit sections, the proximate end of the first section being tapered externally and having an inner wall defining a fluid passage therein, and an annular terminal surface, the proximate end of the second conduit section having an internally conical section tapering off at its proximate end, having an inner wall defining a fluid passage and having an interior ledge at which the fluid passage terminates, the proximate end of the first conduit section fitting into the proximate end of the second conduit section so that with a tight connection of the conduit sections the annular terminal surface is in spaced relation from the interior ledge to provide a fluid receiving space (16) therebetween, said first and second conduit sections together forming a fluid conduit to be filled with a coupling fluid for transmitting a pressure to be measured, one of said conduit sections when filled with said coupling fluid leading via the remote end thereof to a patient for the sensing of the pressure of body fluids, the other of said conduit sections when filled with said coupling fluid leading via the remote end thereof to a pressure sensor, (a) the inner walls defining the fluid passages of said first and second conduit sections being of constant and equal diameter over the entire extent of said fluid conduit between said remote ends except at said fluid receiving space, (b) the fluid receiving space (16) directly adjoining the fluid passages of said constant and equal diameter, an interior wall of the proximate end of said second conduit section defining an outer margin of said fluid receiving space (16) and being of larger diameter than the constant and equal diameter of said fluid passages (10, 11), (c) at least one of said conduit sections (1, 2) having helical groove means (12, 13, 14, 15) formed along the inner wall thereof of said constant and equal diameter and functioning solely to produce rotation of the coupling fluid during filling of said fluid conduit and not for mechanical connection of the fluid conduit, (d) means whereby said helical groove means are of fixed length along said fluid conduit independent of the proximity of the fluid passages of said constant and equal diameter and independent of the degree of tightness of said tight connection, and the fixed length and location of said helical groove means relative to said fluid receiving space (16) being such that the coupling fluid when filled into said fluid conduit from one of said remote ends is caused to rotate as it flows through said fluid receiving space to insure removal of air bubbles from the entirety of said fluid conduit.

2. A conduit as defined in claim 1, characterized by by the fact that at least one of the annular terminal surface (4) of the first conduit section (1) and the interior ledge (7) of the second conduit section (2) is placed obliquely to the longitudinal axis of the conduit.

3. A conduit as defined in claim 1, characterized by the fact that the inner wall (10, 11) of each conduit section (1, 2) is provided with a plurality of grooves (12 to 15) extending therealong.

4. A conduit as defined in claim 3, characterized by the fact that the grooves (12 to 15) of each conduit section (1, 2) continuously taper off in flow cross section from the end to be connected.

5. A conduit as defined in claim 1, characterized by the fact that the helical groove has a relatively large cross section for fluid flow therein where it opens at the space (16) between the surface (4) and ledge (7), and has a progressively decreasing cross section in the direction away from said space (16).

* * * * *